United States Patent [19]

Tsuchiya et al.

[11] Patent Number: 5,959,165
[45] Date of Patent: *Sep. 28, 1999

[54] METHOD AND COMPOSITION FOR INHIBITING DECOMPOSITION OF 1,1,1,2,3,3-HEXAFLUOROPROPANE AND 1,1,1,3,3-PENTAFLUOROPROPANE

[75] Inventors: Tatsumi Tsuchiya; Satoshi Ide, both of Settsu, Japan

[73] Assignee: Daikin Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/945,126

[22] PCT Filed: Apr. 4, 1996

[86] PCT No.: PCT/JP96/00952

§ 371 Date: Oct. 17, 1997

§ 102(e) Date: Oct. 17, 1997

[87] PCT Pub. No.: WO96/33153

PCT Pub. Date: Oct. 24, 1996

[30] Foreign Application Priority Data

Apr. 19, 1995 [JP] Japan .................................. 7-093468

[51] Int. Cl.[6] ................................................... C07C 17/42

[52] U.S. Cl. ........................... 570/110; 570/111; 570/119; 570/121

[58] Field of Search ..................................... 570/110, 111, 570/119, 121

[56] References Cited

U.S. PATENT DOCUMENTS 3,085,116  4/1963  Kvalnes .
3,465,052  9/1969  Okamura et al. .
5,124,503  6/1992  Li ............................................. 570/110

*Primary Examiner*—Alan Siegel
*Attorney, Agent, or Firm*—Larson & Taylor

[57] ABSTRACT

(1) At least one nitro compound and (2) at least one member selected from the group consisting of an aromatic hydrocarbon and an alicyclic unsaturated hydrocarbon are added to 1,1,1,2,3,3-hexafluoropropane (HFC236ea) or 1,1,1,3,3-pentafluoropropane (HFC245fa). Optionally, (3) at least one member selected from the group consisting of an aliphatic unsaturated hydrocarbon, an epoxy compound, an ether compound, a phenol compound, an ester compound and a cyclic compound is further added. As a result, HFC236ea and HFC245fa have remarkably improved stability at any stages and in any states during storage and use of HFC236ea or HFC245fa and during use of the foamed product.

11 Claims, No Drawings

METHOD AND COMPOSITION FOR INHIBITING DECOMPOSITION OF 1,1,1,2,3,3-HEXAFLUOROPROPANE AND 1,1,1,3,3-PENTAFLUOROPROPANE

This application is a 371 of PCT/JP96/00952 filed Apr. 4, 1996.

FIELD OF THE INVENTION

The present invention relates to methods and compositions for inhibiting decomposition of 1,1,1,2,3,3-hexafluoropropane (hereinafter referred to as HFC236ea) and 1,1,1,3,3-pentafluoropropane (hereinafter referred to as HFC245fa). In particular, the invention relates to methods for stabilizing HFC236ea and HFC245fa useful as foaming agents for synthetic resins and inhibiting decomposition thereof, and to decomposition inhibiting compositions preferably usable for said methods.

PRIOR ART

Hydrocarbon halides completely substituted with fluorine or chlorine (hereinafter referred to as fleons) had been widely used as refrigerants, solvents, foaming agents or the like because of their high performance. However, use and production of fleons have been limited since they were found to destroy the ozone layer of the atmosphere of the earth. Accordingly, it is essential to develop novel compounds which can substitute for fleons. Favorable substitutes for fleons include hydrogen-containing hydrocarbon halides (hereinafter referred to as hydrogen-containing fleons) which involves no or low risk of destroying the ozone layer.

Hydrogen-containing fleons so far proposed as foaming agents include 1,1-dichloro-2,2,2-trifluoroethane (HFC-123), 1,1-dichloro-1-fluoroethane (HFC-141b) and the like. However, these compounds, which contain a chlorine atom in the molecule, still have the property of destroying the ozone layer, although the influence is small. In view of these facts, it is necessary to develop a novel foaming agent free from the risk of destroying the ozone layer.

Japanese Unexamined Patent Publication No. 239251/1993 proposes use of HFC236ea and HFC245fa, which are hydrocarbon fluorides free from the risk of destroying the ozone layer, as foaming agents. Hydrogen-containing hydrocarbon halides free from chlorine atoms, although having higher stability than hydrocarbon halides containing chlorine and hydrogen, gradually decompose during storage, transport, etc., giving adverse effects on the production of foamed products.

Japanese Unexamined Patent Publication No. 239251/1993, however, merely suggests use of stabilizers, and does not specify the kinds thereof. It is necessary for the stabilizer to have decomposition inhibiting effects under various conditions. In view of this matter, full consideration should be given to the selection of the stabilizer.

OBJECT OF THE INVENTION

An object of the present invention is to provide a decomposition inhibiting composition which keeps HFC236ea and HFC245fa stable not only during storage but also during the long-term use of the foamed product (such as urethane foam).

DISCLOSURE OF THE INVENTION

The present inventors conducted extensive research in view of the present state of the art as described above, and found that HFC236ea and HFC245fa are stabilized and prevented from being decomposed when mixed with a mixture of a nitro compound and an aromatic hydrocarbon and/or an alicyclic unsaturated hydrocarbon, the mixture optionally containing other specific compound.

They also found that, according to the above method, decomposition of HFC236ea and HFC245fa can be inhibited for a long period under various conditions during storage, transport or use as foaming agents, irrespective of the presence of an alcoholic hydroxyl group-containing compound which promotes decomposition of HFC236ea and HFC245fa. Further, decomposition of HFC236ea and HFC245fa as remaining in the foamed product can be inhibited by the above method. The present invention has been accomplished based on the above novel findings.

The present invention provides a method and composition for inhibiting decomposition of HFC236ea and HFC245fa.

The present invention provides a method for inhibiting decomposition of HFC236ea and HFC245fa, the method comprising adding, to HFC236ea or HFC245fa, (1) at least one nitro compound and (2) at least one member selected from the group consisting of an aromatic hydrocarbon and an alicyclic unsaturated hydrocarbon, optionally together with (3) at least one member selected from the group consisting of an aliphatic unsaturated hydrocarbon, an epoxy compound, an ether compound, a phenol compound, an ester compound and a cyclic nitrogen compound.

The present invention provides a composition for inhibiting decomposition of HFC236ea and HFC245fa, said composition comprising (1) at least one nitro compound and (2) at least one member selected from the group consisting of an aromatic hydrocarbon and an alicyclic unsaturated hydrocarbon (hereinafter this combination is sometimes referred to as the first make-up).

The present invention provides a composition for inhibiting decomposition of HFC236ea and HFC245fa, said composition comprising (1) at least one nitro compound, (2) at least one member selected from the group consisting of an aromatic hydrocarbon and an alicyclic unsaturated hydrocarbon and (3) at least one member selected from the group consisting of an aliphatic unsaturated hydrocarbon, an epoxy compound, an ether compound, a phenol compound, an ester compound and a cyclic nitrogen compound (hereinafter this combination is sometimes referred to as the second make-up).

[1] Decomposition inhibiting composition
(1) Nitro compound

Examples of the nitro compound for use in the present invention include the following aromatic nitro compounds and aliphatic nitro compounds.

Aromatic nitro compound Nitrobenzene, (o-, m-, p-)nitrotoluene, (o-, m-, p-)chloronitrobenzene, (o-, m-)nitrobenzyl alcohol, 4-chloro-3-nitrobenzotrifluoride, m-dinitrobenzene, 2,4-dinitrofluorobenzene, 2,4-dinitrochlorobenzene, p-nitrophenetole, 3-nitrostyrene, 1,2,3-trichloro-4-nitrobenzene, (o-, m-, p-)nitrophenol, (o-, m-, p-) nitroanisole, (m-, p-)fluoronitrobenzene, 2-chloro-6-nitrotoluene, p-nitrophenetole, (2,4-, 2,6-, 3,4-) dinitrotoluene, 2,4-dinitroanisole, 2,4-dinitrophenol, o-nitrobenzyl alcohol, 4-nitrocatechol, etc.

Aliphatic nitro compound

Nitromethane, nitroethane, (1-, 2-) nitropropane, etc. These nitro compounds can be used singly or as a mixture of two or more.

Among the above nitro compounds, nitrobenzene, nitromethane, nitrostyrene and nitrocatechol are particularly preferred.

(2) Aromatic hydrocarbon and alicyclic unsaturated hydrocarbon

Examples of the aromatic hydrocarbon and alicyclic unsaturated hydrocarbon for use in the present invention include the following.

Aromatic hydrocarbon

Styrene, (α-, β-)methylstyrene, p-vinyltoluene, p-isopropenyltoluene, p-diisopropenylbenzene, p-isopropenylxylene, (m-, p-) divinylbenzene, etc.

Alicyclic unsaturated hydrocarbon

Cyclohexadiene, cyclopentadiene, α-pinene, α-limonene, 1,1-diphenylethylene, etc.

The above aromatic hydrocarbons and alicyclic unsaturated hydrocarbons can be used singly or as a mixture of two or more. Among the above examples, aromatic hydrocarbons are preferred, among which (α-, β-) methylstyrene, p-vinyltoluene, p-isopropenyltoluene and p-diisopropenylbenzene are particularly preferred.

(3) Optional compound

The composition of the present invention with the second make-up contains at least one optional compound selected from the group consisting of an aliphatic unsaturated hydrocarbon, an epoxy compound, an ether compound, a phenol compound, an ester compound and a cyclic nitrogen compound, in addition to the nitro compound and the aromatic hydrocarbon and/or alicyclic unsaturated hydrocarbon. Examples of the optional compound include the following.

Aliphatic unsaturated hydrocarbon

Isoprene, 2-methyl-2-butene, 2,3-dimethylbutadiene, 2,3-dimethyl-1-butene, 1,3-pentadiene, 1-hexene, myrcene, etc. Among these aliphatic unsaturated hydrocarbon compounds, isoprene and 2,3-dimethylbutadiene are particularly preferred.

Epoxy compound 1,2-Butyleneoxide, isobutyleneoxide, propylene oxide, epichlorohydrin, styrene oxide, glycidol, etc. Among these epoxy compounds, 1,2-butylene oxide and epichlorohydrin are particularly preferred.

Ether compound 1,4-Dioxane, 1,2-dimethoxyethane, phenylglycidyl ether, allylglycidyl ether, furan, 2,5-dihydrofuran, furil, etc. Among these ether compounds, 1,4-dioxane, phenylglycidyl ether and furan are preferred.

Phenol compound

Phenol, (o-, m-, p-)cresol, (o-, m-, p-)methoxyphenol, thymol, 2,6-di-t-butyl-p-cresol, p-t-butylphenol, eugenol, isoeugenol, anisole, isosafrole, p-t-butylcatechol, etc. Among these phenol compounds, p-t-butylcatechol and 2,6-di-t-butyl-p-cresol are particularly preferred.

Ester compound

Ethyl acrylate, vinyl acrylate, vinyl methacrylate, methyl acetate, methyl salicylate, etc. Among these ester compounds, ethyl acrylate and vinyl methacrylate are particularly preferred.

Cyclic nitrogen compound (N-, 2-, 3-)methylpyrrole, (2-, 4-) vinylpyridine, N-methylmorphorine, benzotriazole, etc. Among these cyclic nitrogen compounds, N-methylpyrrole and 4-vinylpyridine are particularly preferred.

These optional compounds can be used singly or as a mixture of two or more.

In the first make-up of the present invention, a suitable weight ratio of the nitro compound (1) to the aromatic hydrocarbon and/or alicyclic unsaturated hydrocarbon (2) is within the range of 1:9 to 9:1, preferably 2:8 to 8:2, more preferably 3:7 to 7:3.

In the second make-up of the present invention, a suitable weight ratio between the nitro compound (1), the aromatic hydrocarbon and/or alicyclic unsaturated hydrocarbon (2) and the optional compound (3) is within the range of 0.05–5:0.05–5:0.05–5, preferably 0.1–0.5:0.1–0.5:0.1–0.5.

The optional compound (3) for use in the present invention maintains the decomposition inhibiting effect of the nitro compound (1) and the aromatic hydrocarbon and/or alicyclic unsaturated hydrocarbon (2) on HFC236ea and HFC245fa for a long period. If the optional compound is used in an amount smaller than the above range, the decomposition inhibiting effect becomes low, whereas substantial improvement is not obtained by the use of an amount larger than necessary.

[2] Decomposition inhibiting method (1) The nitro compound (1) and the aromatic hydrocarbon and/or alicyclic unsaturated hydrocarbon (2) are suitably used in a total amount of 0.1 to 5 wt. parts, preferably 0.2 to 1 wt. parts, per 100 wt. parts of HFC236ea or HFC245fa. The proportion of the nitro compound (1) and the aromatic hydrocarbon and/or alicyclic unsaturated hydrocarbon (2) are 0.05 to 5 wt. parts, preferably 0.1 to 0.5 wt. parts of the former and 0.05 to 5 wt. parts, preferably 0.1 to 0.5 wt. parts of the latter.

If the nitro compound (1) and the aromatic hydrocarbon and/or alicyclic unsaturated hydrocarbon (2) are used in amounts smaller than the above range, the decomposition inhibiting effect on HFC236ea and HFC245fa becomes insufficient, whereas substantial improvement is not obtained by the use of an amount larger than necessary.

The composition of the present invention with the second make-up is used in an amount of 0.15 to 5 wt. parts, preferably 0.3 to 1 wt. parts per 100 wt. parts of HFC236ea or HFC245fa. The proportions of the three components are 0.05 to 5 wt. parts, preferably 0.1 to 0.5 wt. parts of the nitro compound (1), 0.05 to 5 wt. parts, preferably 0.1 to 0.5 wt. parts of the aromatic hydrocarbon and/or alicyclic unsaturated hydrocarbon (2), and about 0.05 to 5 wt. parts, preferably 0.1 to 1 wt. parts of the optional compound (3).

There is no specific limitation on the method of adding the nitro compound (1), the aromatic hydrocarbon and/or alicyclic unsaturated hydrocarbon (2) and the optional compound (3) as stabilizer components to HFC236ea or HFC245fa to be stabilized. The stage and method for addition can be suitably selected according to the purpose of use and intended use of HFC236ea and HFC245fa, other substances to be used in combination with HFC236ea or HFC245fa, temperatures during storage, production of the foamed product and use of the product, and other factors.

The composition and method for inhibiting decomposition according to the present invention are effective not only when HFC236ea or HFC245fa is used singly as a foaming agent, but also when HFC236ea and HFC245fa are used as a mixture or in combination with other foaming agents or water. The following foaming agents can be used in combination with HFC236ea or HFC245fa when carrying out the decomposition inhibiting method of the invention.

Hydrogen-containing fluorohydrocarbon (HFC)

Difluoroethane (32), difluoroethane (152), trifluoroethane (143), tetrafluoroethane (134), heptafluoropropane (227), hexafluoropropane (236), pentafluoropropane (245), hexafluorobutane (356), etc. Isomers of the above hydrogen-containing fluorohydrocarbons, if present, can be used singly or as a mixture, in combination with HFC236ea.

Low-boiling hydrocarbon halide

Trichloromonofluoromethane, dichlorodifluoromethane, methylene chloride, perfluoropentane, etc.

Low-boiling hydrocarbon n-Pentane, isopentane, cyclopentane, n-butane, isobutane, etc.

Inert gas

Air, nitrogen, carbon dioxide gas, etc.

(2) Foamed heat insulating material

The composition and method of the invention are particularly useful for inhibiting decomposition of HFC236ea and HFC245fa used as foaming agents for producing foamed heat insulating materials. The method and composition of the invention can be employed for conventional processes for producing foamed heat insulating material. In such processes, decomposition of HFC236ea and HFC245fa can be inhibited when HFC236ea or HFC245fa is mixed with the decomposition inhibiting composition of the invention and used as a foaming agent.

Other starting materials for producing the foamed heat insulating material may be those known. For example, for producing polyurethane foam, organic isocyanates, polyols, catalysts and additives may be used. Specific examples of these additives are as follows.

Usable organic isocyanates include aliphatic, alicyclic and aromatic isocyanates as described in Keiji IWATA, "Polyurethane Resin Handbook", Nikkan Kogyo Shinbunsha, pages 71 to 98.

The most generally used polyisocyanates include 2,4-tolylenediisocyanate(2,4-TDI) and 2,6-tolylenediisocyanate (2,6-TDI), which are mainly used as a mixture having the 2,4-TDI/2,6-TDI ratio of 80/20 or 65/35. Also used as the polyisocyanate are polyphenyl-polymethylene polyisocyanate (crude MDI) obtained by making a condensate of aniline and formaldehyde react with phosgen.

Usable polyols include polyether polyols and polyester polyols [Keiji IWATA, "Polyurethane Resin Handbook", Nikkan Kogyo Shinbunsha, pages 99 to 117].

Polyether polyols can be obtained by the reaction of alkylene oxide with an initiator having an active hydrogen atom. In the present invention, polyether polyols having 2 to 8 functional groups and a hydroxyl value of 300 to 600 mg KOH/g can be used, which is obtained by reacting ethylene glycol, trimethylolpropane, glycerine, triethanolamine, ethylenediamine, methylglucoside, tolylenediamine, sorbitol, sucrose or like initiator with ethylene oxide, propylene oxide or like alkylene oxide.

Examples of the polyester polyols are condensed polyester polyols obtained by dehydration condensation of adipic acid with glycol or toluol, lactone-based polyesters obtained by ring-opening polymerization of caprolactam, polycarbonate diol and the like. Among them, those having 2 to 4 functional groups and a hydroxyl value of 250 to 500 mg KOH/g can be used in the present invention.

Usable catalysts include tertiary amines, organic metal compounds and mixtures thereof. The catalyst is used usually in an amount of 0.01 to 10 wt. %, preferably about 0.1 to 5 wt. %, based on the total amount of the foaming materials (organic isocyanate, polyol and foaming agent).

Tertiary amines usable as the catalyst are monoamines such as triethylamine and dimethylcyclohexylamine, diamines such as tetramethylethylenediamine and tetramethylhexamethylenediamine, cyclic amines such as triethylenediamine and 1,2-dimethylimidazole, alcohol amines such as dimethylaminoethanol, and the like. Examples of the organic metal compounds are stannous octoate, dibutyltin dilaurate, dibutyltin diacetate, octenoic acid and the like.

Other additives for producing polyurethane foam include silicone-based or fluorine-containing surfactants for use as surfactant. Specific examples of the surfactants are those comprising as the base polysiloxane-polyalkylene blocked copolymers, methylpolysiloxane or the like.

When necessary, conventional fillers, coloring agents, fire retardants, mildewproofing agents, release agents and the like can be used as additives.

Effects of the invention

According to the present invention, HFC236ea and HFC245fa have remarkably improved stability at any stages and in any states during storage, transport and use of HFC236ea or HFC245fa, and during use of the foamed products. According to the present invention, decomposition of HFC236ea and HFC245fa can be inhibited even when HFC236ea or HFC245fa is used in the presence of a compound containing an alcoholic hydroxyl group.

The composition of the present invention has an excellent decomposition inhibiting effect on HFC236ea and HFC245fa. Therefore, when said composition is employed in the production of foamed heat insulating material (polyurethane foam) using HFC236ea or HFC245fa as a foaming agent, HFC236ea and HFC245fa can be effectively prevented from being decomposed at any stages and in any states during storage of the starting materials, during production of a foamed insulating material using HFC236ea or HFC245fa as a foaming agent and during use of the foamed product (polyurethane foam). As a result, the obtained polyurethane foam has improved dimensional stability and uniform cell size.

Accordingly, the decomposition inhibiting method of the present invention is practically very useful for inhibiting decomposition of HFC236ea and HFC245fa, in particular, inhibiting decomposition of HFC236ea and HFC245fa used as foaming agents for producing foamed heat insulating materials.

EXAMPLES

The following Examples and Comparative Examples illustrate the present invention in further detail.

Examples 1 to 19 and Comparative Examples 1 to 14

The starting materials used in the Examples and Comparative Examples are as follows.

Polyol: o-Tolylenediamine-based polyether polyol having a hydroxyl value of 400 mg KOH/g Surfactant: Silicon-based surfactant manufactured by Toray Silicone Co., Ltd, available under the trademark "SH-193"

Catalyst: Tetramethylhexamethylenediamine

Foaming agent: 1,1,1,2,3,3-Hexafluoropropane

Organic isocyanate: Polyphenylpolymethylene-polyisocyanate (crude MDI)

Decomposition inhibiting composition (1) Nitro compound

A: Nitrobenzene

B: Nitromethane

C: Nitrostyrene

D: Nitrocatechol (2) Aromatic hydrocarbon

E: α-methylstyrene

F: p-isopropenyltoluene

G: p-diisopropenylbenzene (3) Combination of nitro compound and aromatic hydrocarbon H: Nitrobenzene (0.4 wt. parts) and p-isopropenyltoluene (0.4 wt. parts)

(4) Optional compound
I: Isoprene
J: 1,2-Butylene oxide
K: 1,4-Dioxane
L: 2,6-Di-t-butyl-p-cresol (BHT)
M: Ethyl acrylate
N: N-Methylpyrrol A mixture for producing rigid polyurethane foam was prepared which consisted of the polyol (100 wt. parts), the surfactant (1.5 wt. parts), the catalyst (3.4 wt. parts), the foaming agent (39 wt. parts) and a decomposition inhibiting composition consisting of the component(s) shown in Tables 1 or 2 in the amount(s) (wt. parts) shown therein. The organic isocyanate (71 wt. parts) was added to the obtained mixture (100 wt. parts), followed by hand-mixing to give polyurethane foam. The obtained polyurethane foam was aged for 1 day and cut into 10 cm cubes, and each cube was vacuum-packed with an aluminum laminate.

One of the packed polyurethane foam cubes was pressed with a pressing machine to determine, by gas chromatography, the concentrations of decomposition gases, i.e., $CF_3CH=CF_2$ (1,1,3,3,3-pentafluoropropylene, product A) and CF CFHCFH (1,1,1,2,3-pentafluoropropane, product B) produced during the exothermic reaction on the foaming of urethane. The decomposition inhibiting effect, i.e., performance as a decomposition inhibiting composition, on HFC236ea during the foaming reaction was thus tested.

Another packed polyurethane foam cube was allowed to stand in an atmosphere at 90° C. for 2 weeks and pressed with a pressing machine in the same manner as above to determine, by gas chromatography, the concentrations of the decomposition gases produced during aging. The results are shown in Tables 1 and 2.

TABLE 1

| Decomposition inhibiting composition Kind (Amount) | Decomposition gas concentration (ppm) | | | |
|---|---|---|---|---|
| | During reaction | | During aging | |
| | Product A | Product B | Product A | Product B |
| Comp. Ex. 1 | — | 90 | 50 | 1000 | 250 |
| Comp. Ex. 2 | A (1.0) | 0 | 0 | 100 | 25 |
| Comp. Ex. 3 | B (1.0) | 0 | 0 | 110 | 30 |
| Comp. Ex. 4 | C (1.0) | 0 | 0 | 115 | 30 |
| Comp. Ex. 5 | D (1.0) | 0 | 0 | 110 | 30 |
| Comp. Ex. 6 | E (1.0) | 0 | 0 | 140 | 35 |
| Comp. Ex. 7 | F (1.0) | 0 | 0 | 150 | 40 |
| Comp. Ex. 8 | G (1.0) | 0 | 0 | 150 | 40 |
| Ex. 1 | A (0.5) E (0.5) | 0 | 0 | 70 | 20 |
| Ex. 2 | A (0.5) F (0.5) | 0 | 0 | 40 | 10 |
| Ex. 3 | A (0.5) G (0.5) | 0 | 0 | 75 | 20 |
| Ex. 4 | B (0.5) E (0.5) | 0 | 0 | 50 | 10 |
| Ex. 5 | B (0.5) F (0.5) | 0 | 0 | 75 | 15 |
| Ex. 6 | B (0.5) G (0.5) | 0 | 0 | 80 | 20 |
| Ex. 7 | C (0.5) E (0.5) | 0 | 0 | 75 | 15 |
| Ex. 8 | C (0.5) F (0.5) | 0 | 0 | 80 | 20 |
| Ex. 9 | C (0.5) G (0.5) | 0 | 0 | 80 | 20 |
| Ex. 10 | D (0.5) E (0.5) | 0 | 0 | 80 | 20 |

TABLE 1-continued

| Decomposition inhibiting composition Kind (Amount) | Decomposition gas concentration (ppm) | | | |
|---|---|---|---|---|
| | During reaction | | During aging | |
| | Product A | Product B | Product A | Product B |
| Ex. 11 | D (0.5) F (0.5) | 0 | 0 | 90 | 20 |
| Ex. 12 | D (0.5) G (0.5) | 0 | 0 | 80 | 20 |

TABLE 2

| Decomposition inhibiting composition Kind (Amount) | Decomposition gas concentration (ppm) | | | |
|---|---|---|---|---|
| | During reaction | | During aging | |
| | Product A | Product B | Product A | Product B |
| Ex. 13 | H (0.8) | 0 | 0 | 45 | 15 |
| Ex. 14 | H (0.8) I (0.2) | 0 | 0 | 0 | 0 |
| Ex. 15 | H (0.8) J (0.2) | 0 | 0 | 0 | 0 |
| Ex. 16 | H (0.8) K (0.2) | 0 | 0 | 5 | 0 |
| Ex. 17 | H (0.8) L (0.2) | 0 | 0 | 0 | 0 |
| Ex. 18 | H (0.8) M (0.2) | 0 | 0 | 10 | 5 |
| Ex. 19 | H (0.8) N (0.2) | 0 | 0 | 10 | 5 |
| Comp. Ex. 9 | I (0.2) | 45 | 15 | 750 | 180 |
| Comp. Ex. 10 | J (0.2) | 45 | 15 | 750 | 180 |
| Comp. Ex. 11 | K (0.2) | 55 | 20 | 780 | 190 |
| Comp. Ex. 12 | L (0.2) | 45 | 15 | 680 | 180 |
| Comp. Ex. 13 | M (0.2) | 55 | 20 | 780 | 190 |
| Comp. Ex. 14 | N (0.2) | 55 | 20 | 790 | 190 |

Examples 20 to 38 and Comparative Examples 15 to 28

The same starting materials as used in Examples 1 to 19 and Comparative Examples 1 to 14 were used with the exception that 1,1,1,3,3-pentafluoropropane was used as the foaming agent.

A mixture for producing rigid polyurethane foam was prepared which consisted of the polyol (100 wt. parts), the surfactant (1.5 wt. parts), the catalyst (3.4 wt. parts), the foaming agent (34 wt. parts) and a decomposition inhibiting composition consisting of the component(s) shown in Tables 3 or 4 in the amount(s) (wt. parts) shown therein. The organic isocyanate (71 wt. parts) was added to the obtained mixture (100 wt. parts), followed by hand-mixing to give polyurethane foam. The obtained polyurethane foam was aged for 1 day and cut into 10 cm cubes, and each cube was vacuum-packed with an aluminum laminate.

One of the packed polyurethane foam cubes was pressed with a pressing machine to determine, by gas chromatography, the concentrations of decomposition gases, i.e., $CF_3CH=CFH$ (1,3,3,3-tetrafluoropropylene, product A) and $CF_3CH_2CFH_2$ (1,1,1,3-tetrafluoropropane, product B) produced during the exothermic reaction on the foaming of urethane. The decomposition inhibiting effect, i.e., performance as a decomposition inhibiting composition, on HFC245fa during the foaming reaction was thus tested.

Another packed polyurethane foam cube was allowed to stand in an atmosphere at 90° C for 2 weeks and pressed with a pressing machine in the same manner as above to determine, by gas chromatography, the concentrations of the decomposition gases produced during aging. The results are shown in Tables 3 and 4.

TABLE 3

| Decomposition inhibiting composition Kind (Amount) | Decomposition gas concentration (ppm) | | | |
|---|---|---|---|---|
| | During reaction | | During aging | |
| | Product A | Product B | Product A | Product B |
| Comp. Ex. 15 | — | 60 | 30 | 800 | 200 |
| Comp. Ex. 16 | A (1.0) | 0 | 0 | 80 | 20 |
| Comp. Ex. 17 | B (1.0) | 0 | 0 | 90 | 25 |
| Comp. Ex. 18 | C (1.0) | 0 | 0 | 95 | 25 |
| Comp. Ex. 19 | D (1.0) | 0 | 0 | 120 | 30 |
| Comp. Ex. 20 | E (1.0) | 0 | 0 | 130 | 35 |
| Comp. Ex. 21 | F (1.0) | 0 | 0 | 130 | 35 |
| Comp. Ex. 22 | G (1.0) | 0 | 0 | 130 | 35 |
| Ex. 20 | A (0.5) E (0.5) | 0 | 0 | 50 | 15 |
| Ex. 21 | A (0.5) F (0.5) | 0 | 0 | 20 | 5 |
| Ex. 22 | A (0.5) F (0.5) | 0 | 0 | 55 | 15 |
| Ex. 23 | B (0.5) E (0.5) | 0 | 0 | 30 | 5 |
| Ex. 24 | B (0.5) F (0.5) | 0 | 0 | 55 | 10 |
| Ex. 25 | B (0.5) G (0.5) | 0 | 0 | 60 | 15 |
| Ex. 26 | C (0.5) E (0.5) | 0 | 0 | 55 | 10 |
| Ex. 27 | C (0.5) F (0.5) | 0 | 0 | 60 | 15 |
| Ex. 28 | C (0.5) G (0.5) | 0 | 0 | 60 | 15 |
| Ex. 29 | D (0.5) E (0.5) | 0 | 0 | 60 | 15 |
| Ex. 30 | D (0.5) F (0.5) | 0 | 0 | 65 | 15 |
| Ex. 31 | D (0.5) G (0.5) | 0 | 0 | 60 | 15 |

TABLE 4

| Decomposition inhibiting composition Kind (Amount) | Decomposition gas concentration (ppm) | | | |
|---|---|---|---|---|
| | During reaction | | During aging | |
| | Product A | Product B | Product A | Product B |
| Ex. 32 | H (0.8) | 0 | 0 | 30 | 10 |
| Ex. 33 | H (0.8) I (0.2) | 0 | 0 | 0 | 0 |
| Ex. 34 | H (0.8) J (0.2) | 0 | 0 | 0 | 0 |
| Ex. 35 | H (0.8) K (0.2) | 0 | 0 | 5 | 0 |
| Ex. 36 | H (0.8) L (0.2) | 0 | 0 | 0 | 0 |
| Ex. 37 | H (0.8) M (0.2) | 0 | 0 | 10 | 5 |
| Ex. 38 | H (0.8) N (0.2) | 0 | 0 | 10 | 5 |
| Comp. Ex. 23 | I (0.2) | 35 | 10 | 600 | 150 |
| Comp. Ex. 24 | J (0.2) | 35 | 15 | 620 | 150 |
| Comp. Ex. 25 | K (0.2) | 45 | 15 | 700 | 160 |
| Comp. Ex. 26 | L (0.2) | 35 | 10 | 600 | 150 |
| Comp. Ex. 27 | M (0.2) | 45 | 15 | 700 | 160 |
| Comp. Ex. 28 | N (0.2) | 45 | 15 | 700 | 160 |

We claim:

1. A method for inhibiting decomposition of 1,1,1,2,3,3-hexafluoropropane and 1,1,1,3,3-pentafluoropropane, the method comprising adding (1) at least one nitro compound and (2) at least one aromatic hydrocarbon to 1,1,1,2,3,3-hexafluoropropane or 1,1,1,3,3-pentafluoropropane.

2. A method for inhibiting decomposition of 1,1,1,2,3,3-hexafluoropropane and 1,1,1,3,3-pentafluoropropane, the method comprising adding (1) at least one nitro compound, (2) at least one aromatic hydrocarbon and (3) at least one phenol compound to 1,1,1,2,3,3-hexafluoropropane or 1,1,1,3,3-pentafluoropropane.

3. A composition for inhibiting decomposition of 1,1,1,2,3,3-hexafluoropropane and 1,1,1,3,3-pentafluoropropane, the composition comprising (1) at least one nitro compound and (2) at least one aromatic hydrocarbon.

4. A composition for inhibiting decomposition of 1,1,1,2,3,3-hexafluoropropane and 1,1,1,3,3-pentafluoropropane, the composition comprising (1) at least one nitro compound, (2) at least one aromatic hydrocarbon and (3) at least one phenol compound.

5. A composition for inhibiting decomposition of 1,1,1,2,3,3-hexafluoropropane and 1,1,1,3,3-pentafluoropropane according to claim 3, wherein (1) the nitro compound is selected from the group consisting of nitrobenzene, nitromethane, nitrostyrene and nitrocatechol.

6. A composition for inhibiting decomposition of 1,1,1,2,3,3-hexafluoropropane and 1,1,1,3,3-pentafluoropropane according to claim 3, wherein (2) the aromatic hydrocarbon is selected from the group consisting of α-methylstyrene, β-methylstyrene, p-vinyltoluene, p-isopropenyltoluene and p-diisopropenylbenzene.

7. A composition for inhibiting decomposition of 1,1,1,2,3,3-hexafluoropropane and 1,1,1,3,3-pentafluoropropane according to claim 3, wherein (1) the nitro compound is nitrobenzene and (2) the aromatic hydrocarbon is p-isopropenyltoluene.

8. A composition for inhibiting decomposition of 1,1,1,2,3,3-hexafluoropropane and 1,1,1,3,3-pentafluoropropane according to claim 4, wherein (1) the nitro compound is nitrobenzene, (2) the aromatic hydrocarbon is p-isopropenyltoluene and (3) the phenol compound is 2,6-di-t-butyl-p-cresol.

9. A composition for inhibiting decomposition of 1,1,1,2,3,3-hexafluoropropane and 1,1,1,3,3-pentafluoropropane according claim 4, wherein (1) the nitro compound is selected from the group consisting of nitrobenzene, nitromethane, nitrostyrene and nitrocatechol.

10. A composition for inhibiting decomposition of 1,1,1,2,3,3-hexafluoropropane and 1,1,1,3,3-pentafluoropropane according to claim 4, wherein (2) the aromatic hydrocarbon is selected from the group consisting of α-methylstyrene, β-methylstyrene, p-vinyltoluene, p-isopropenyltoluene and p-dissopropenylbenzene.

11. A composition for inhibiting decomposition of 1,1,1,2,3,3-hexafluoropropane and 1,1,1,3,3-pentafluoropropane according to claim 4, wherein (1) the nitro compound is nitrobenzene and (2) the aromatic hydrocarbon is p-isopropenyltoluene.

* * * * *